(12) United States Patent
Rankin

(10) Patent No.: US 10,702,731 B2
(45) Date of Patent: Jul. 7, 2020

(54) UPPER BODY HARNESS WITH ELASTIC BANDS FOR RESISTANCE EXERCISES

(71) Applicant: Global Industry Products, Corp., Las Vegas, NV (US)

(72) Inventor: James Terrell Rankin, Henderson, NV (US)

(73) Assignee: Global Industry Products, Corp., Las Vegas, NV (US)

( * ) Notice: Subject to any disclaimer, the term of this patent is extended or adjusted under 35 U.S.C. 154(b) by 0 days.

(21) Appl. No.: 16/184,872

(22) Filed: Nov. 8, 2018

(65) Prior Publication Data

US 2019/0168055 A1 Jun. 6, 2019

Related U.S. Application Data

(60) Provisional application No. 62/707,576, filed on Nov. 9, 2017.

(51) Int. Cl.
| | | |
|---|---|---|
| A63B 21/04 | (2006.01) | |
| A63B 21/00 | (2006.01) | |
| A63B 21/055 | (2006.01) | |
| A63B 23/12 | (2006.01) | |
| A63B 1/00 | (2006.01) | |

(52) U.S. Cl.
CPC ............ *A63B 21/0442* (2013.01); *A63B 1/00* (2013.01); *A63B 21/00061* (2013.01); *A63B 21/0555* (2013.01); *A63B 21/0557* (2013.01); *A63B 21/4007* (2015.10); *A63B 21/4035* (2015.10); *A63B 23/1209* (2013.01); *A63B 2209/00* (2013.01); *A63B 2225/09* (2013.01)

(58) Field of Classification Search
CPC ........ A63B 21/04–0557; A63B 21/4001–4021
See application file for complete search history.

(56) References Cited

U.S. PATENT DOCUMENTS

| | | | | |
|---|---|---|---|---|
| 4,911,439 A | * | 3/1990 | Kuhl .................. | A63B 21/0552 482/124 |
| 5,662,563 A | | 9/1997 | Maerzke | |
| 5,792,034 A | * | 8/1998 | Kozlovsky ......... | A63B 21/0004 482/124 |
| 7,854,694 B1 | | 12/2010 | Frunzi | |
| 2003/0125170 A1 | | 7/2003 | Vernon | |
| 2005/0282689 A1 | | 12/2005 | Weinstein | |
| 2009/0062087 A1 | * | 3/2009 | Poppinga ........... | A63B 21/0552 482/124 |
| 2012/0329617 A1 | * | 12/2012 | Tal ..................... | A63B 21/0414 482/124 |
| 2018/0021624 A1 | * | 1/2018 | Cordero ................. | A63B 23/12 601/48 |
| 2018/0200557 A1 | * | 7/2018 | Prospero ............ | A63B 21/0552 |

OTHER PUBLICATIONS

International Search Report and Written Opinion for PCT Application No. PCT/US18/59956.

* cited by examiner

*Primary Examiner* — Jennifer Robertson
(74) *Attorney, Agent, or Firm* — IRL Legal Services, LLC; Ilya R. Lapshin

(57) ABSTRACT

An exercise and training device comprising a sleeved chest harness to which stretchable straps with handles are attached.

16 Claims, 2 Drawing Sheets

UPPER BODY HARNESS WITH ELASTIC BANDS FOR RESISTANCE EXERCISES

RELATED APPLICATIONS

This application claims the benefit under 35 USC 119(e) of U.S. Provisional Applications No. 62/707,576, filed on Nov. 9, 2017, which is incorporated herein by reference in its entirety.

FIELD OF THE INVENTION

The invention pertains to exercise equipment, cardio training, equipment for sports training (for example, for boxing), equipment for building strength, and to the similar devices and methods.

BACKGROUND

The use of stretchable elastic bands for various exercises is known in the art.

SUMMARY

Some embodiments provide a combination of a posture-correcting shoulder or chest harness, wearable replaceable resistance straps or bands (such as Thera-Bands) for kinetic-energy-based low-impact resistance exercise, and a heart-monitoring system or systems.

An example embodiment comprises a posture-correcting shoulder harness comprising: a first sleeve positionable around a shoulder and an adjacent armpit of the user; a second sleeve positionable around another shoulder and another armpit of the user; and a back support connecting a posterior part of the first sleeve and a posterior part of the second sleeve behind the back of the user; and a first stretchable strap comprising: a first portion attached to the harness; and a first handle positioned on the first strap distantly from the first portion of the first strap.

Another example embodiment comprises a chest harness comprising: a first sleeve positionable around a shoulder and an adjacent armpit of the user; a second sleeve positionable around another shoulder and another armpit of the user; and a back support connecting a posterior part of the first sleeve and a posterior part of the second sleeve behind the back of the user; and a first stretchable strap threaded through the harness and comprising a first handle positioned on the first strap distantly from the harness.

Some embodiments further comprise a second stretchable strap comprising: a first portion attached to the harness; and a second handle positioned on the second strap distantly from the first portion of the second strap to allow the user to hold the first handle with one hand and hold the second handle with another hand.

In some embodiments, the back support further comprises a back-support plate positionable against the back of the user.

In some embodiments, the first portion is detachably attached to the harness.

In some embodiments, the first portion of the first strap is attached to the front portion of the first sleeve.

In some embodiments, the first strap further comprises a second portion attached to the harness; and the first handle is positioned on the first strap distantly from the second portion of the first strap.

In some embodiments, the first strap comprises an elastic band.

In some embodiments, the first strap is loop-shaped.

In some embodiments, the first portion is attached to the harness by threading the first portion through at least one opening in the harness.

In some embodiments, the first handle is movably positioned on the first strap.

In some embodiments, the first portion of the first strap is attached to the back support.

Some embodiments further comprise a second handle positioned on the first strap distantly from the first handle and distantly from the harness.

Some embodiments further comprise a front chest strap connecting the first sleeve with the second sleeve in front of the user.

In some embodiments, the harness is posture-correcting.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

All illustrations of the drawings are for the purpose of describing selected versions of the present invention and are not intended to limit the scope of the present invention.

DETAILED DESCRIPTION

Figure 1:
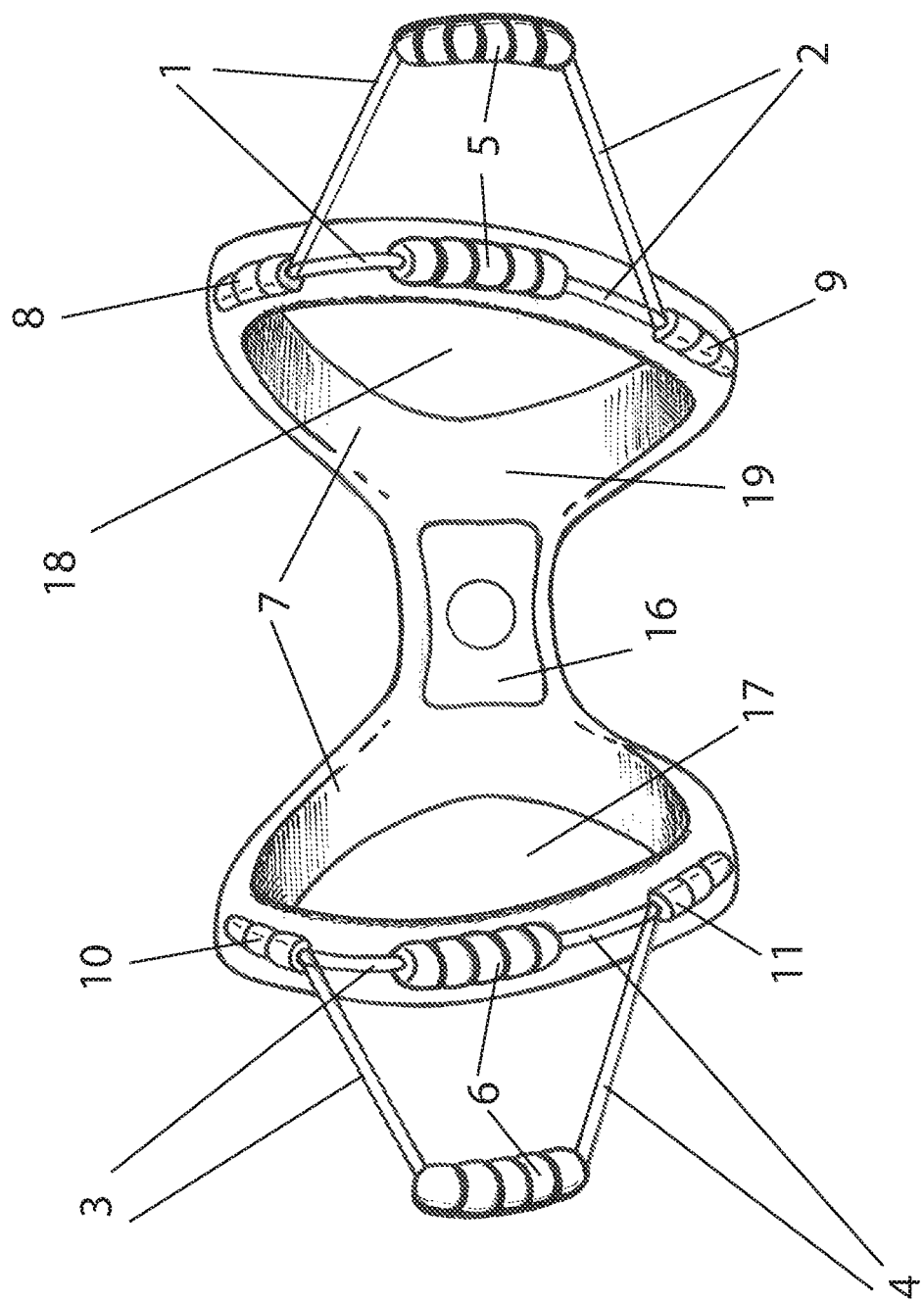
FIG. 1 shows a front view of an embodiment of the present invention.

An embodiment shown in FIG. 1 is a sports training (including boxing training), cardio exercise, and muscle building device, which may include a shoulder and posture harness or vest 7 (incorporating a back support 19) with bands or straps 1, 2, 3, and 4, which may include any available stretchable or elastic band, strip, or cord, including ones using the Thera-Band technologies. The straps 1, 2, 3, and 4 are shown in two states or positions—a retracted/rested position closer to the harness 7 and an extended/punching position further from the harness 7—the difference being more or less tension or extension applied to the strap through the handles 5 and 6 (also shown in two states or positions). The handles 5 and 6 are possibly made with a soft material. The handles 5 and 6 are held or grasped by users who may exercise or train their arms by extending their arms (for example, in a punching motion or a pushing motion) against the elastic resistance of the straps against stretching forces.

The straps 1 and 2 may be one continuous strap threaded through a hole in the handle 5. Such handle 5 may slide on the strap. The same is true for the straps 3 and 4 and the handle 6.

The strap 1 may be connected, anchored, threaded, or attached to the harness 7 at locations 8 and 9 (which may be the same location, or which may be optionally located one above the other) on one side of the harness 7 to provide two points of resistance. The straps 1 and 2 may be connected to the harness 7 outside of the user's shoulder area or inner minor deltoids and the outer pectoral muscles. The location 8 may be above or atop the shoulder or deltoid resting on the outer trapezius. The location 9 may be below/under the arm resting on the outer stratus and latissimus dorsi muscles.

The connections at the location 8 and 9 may be permanent or be formed by clips or buckles (including, for example, parachute-quality snap buckles, where the male parts of the buckles are attached to straps and the female parts of the buckles are attached to the harness 7 to increase the device's strength and to provide for its long-lasting performance and durability) which may enable the user to attach and reattach the straps 1 and 2 and to replace the straps 1 and 2 with interchangeable straps having different tension, extensions resistance or elasticity (for example, light, medium, or heavy) depending on the user's strength capability or exercise desire or need.

Alternatively, the straps 1 and 2 may be connected by threading them through the harness; in this case they may form one continuous strap, which may be loop-shaped so that the handle 5 may slide on this loop-shaped strap. The same is true for the straps 3 and 4, the handle 6, and positions 10 and 11.

The user may grab the handles 5 and 6 positioned on the strap resting at about chest height and perform the boxing motion or punching forward at opposite times, with each hand and arm performing a corkscrew motion by turning or rolling over the hand as the user extends the arm to finish the punch motion. This motion was developed for a more efficient and stronger finishing punch in boxing.

Some embodiments may include a strap or straps with a handle only on the left side or only on the right side of the harness for single-arm exercises.

Alternatively, a single strap 1, without the second strap 2, may be attached to the harness 7 by one end at the location 8, with the handle 5 attached to the strap 1 on or near the opposite end of the strap 1.

A back-support plate 16 possibly centered on the back support 19 of harness 7 supports the tension by giving more strength and stability while the user is pulling on straps on either side.

Figure 2:
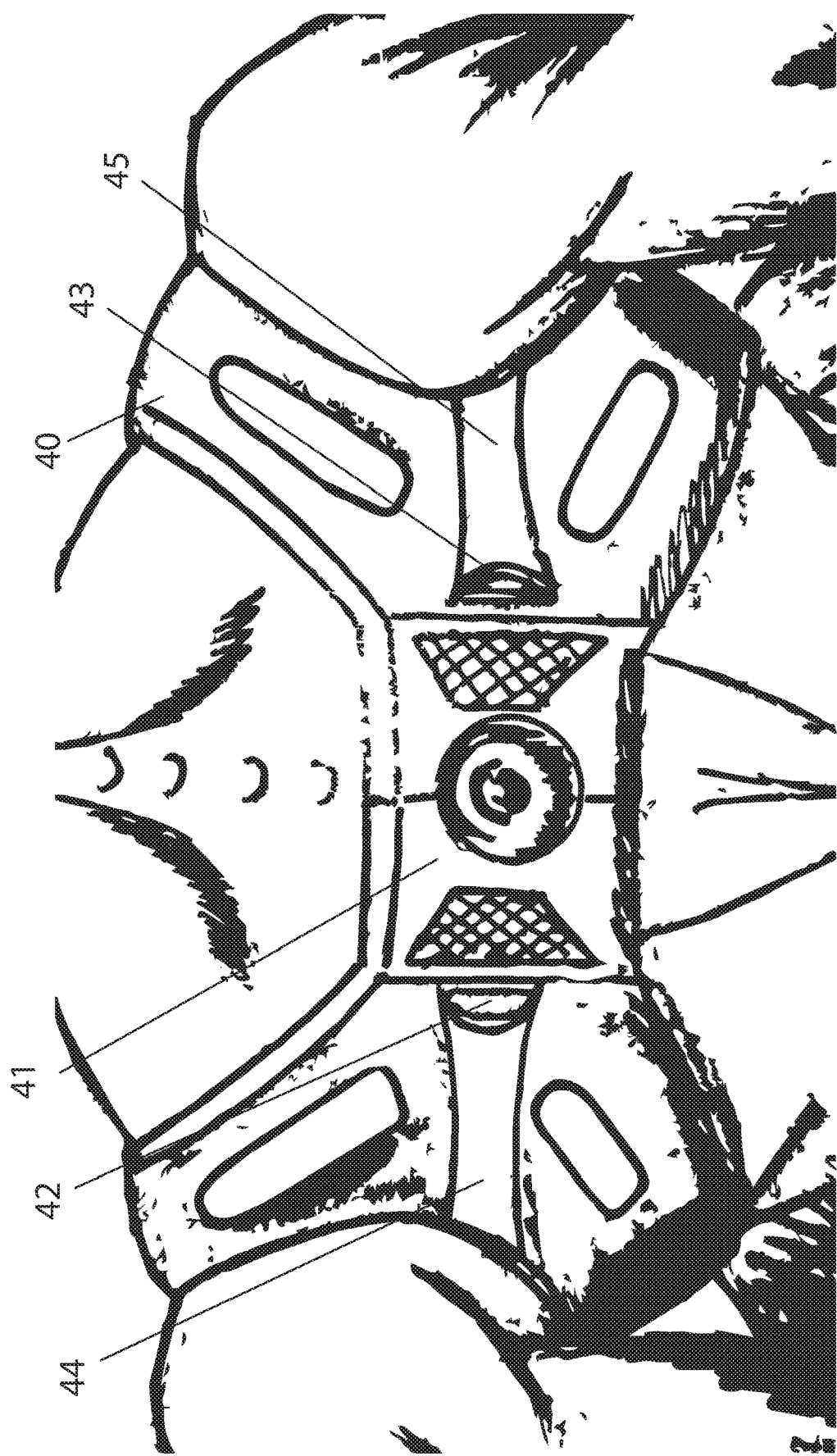
FIG. 2 shows a back view of an embodiment of the present invention.

FIG. 2 shows a back view of an embodiments where the straps 44 and 45 are attached to the back support 41 of the harness 40 with the buckles 42 and 43. Each strap may be replaced by a pair of straps, as discussed hereinabove.

Alternatively, the straps 44 and 45 may form one continuous strap threaded through holes in the harness 40 (for example, through its back support 41).

Alternatively, threaded through holes in the harness 40 (for example, through its back support 41) may be a strap shaped as a continuous loop, one half of the loop being on the right, another half, on the left, with two handles slidably positioned on this loop-shaped strap.

The harness 7 slides and sits on the user's shoulders (using the sleeves 17 and 18 fitting around the user's shoulders and underarms) and may include an upper cardio belt that fastens around the user's lower chest cavity or a front chest strap connecting the sleeves in from of the user.

The device may include a battery-operated heart monitoring system having cardio sensors embedded in the inner lining of the edge of a chest belt and/or into the shoulder straps preferably close to the axillary and brachial arteries for heart and/or pulse reading. These sensors take and monitor the user's heart rate while the user runs and/or exercises. The heart monitoring system may include an LED read-out badge or a display box at the center of the chest strap or clip that may display the numeric heart rate and may include LEDs blinking of flashing in sync with the user's heart rate. The batteries, sensors, LED badges, or display boxes used for the heart monitoring may be changeable and/or replaceable.

The harness may accommodate a variety of devices or parts attachable via a female receptor on the harness for a male clip or snap buckle connected to a water pouch or a water holding system (for example, a Camel Pack) with attached drinking straw allowing drinking while the water container is worn on the back.

The harness and/or the back-support plate may also provide support for a variety of attachments, such as a mini back-pack, an LED light, a phone or a music player holder, added weights, etc.

Reflective tape or LED lights or strips may be attached to the harness for the user's safety when the device is used outdoors, especially at night for visual safety precautions.

Pockets and pouches (possibly made of spandex) may be attached to the harness to allow the user to keep a phone, keys, wallet, or other smaller items, devices, and necessities needed or used during exercising, running, or walking.

If the user replaces the straps with longer or shorter straps, the result may be that the straps are too loose or slack or too tight and resistant. Some embodiments may include additional strap buckles or hooks for the upper and/or lower shoulder straps. These additional strap buckles or hooks allow the user to adjust the straps on both sides of the harness. By using the differently placed hooks or buckles, the user may move the straps up to tighten or down to loosen them for a more perfect fit when working out.

Some embodiments may include additional padding or rubber on the harness's shoulders, back, and straps to provide more comfort, strength, and rigidness if necessary for performance and durability and/or for aesthetic appearance.

The device may utilize light-weight breathable elastic nylon in a variety of colors over thin neoprene material with foam lining for comfort and stability.

Although the invention has been explained in relation to its preferred embodiment, it is to be understood that many other possible modifications and variations can be made without departing from the spirit and scope of the invention as hereinafter claimed. While this invention has been particularly shown and described with references to preferred embodiments thereof, it will be understood by those skilled in the art that various changes in form and details may be made therein without departing from the scope of the invention encompassed by the appended claims.

The invention claimed is:

1. An exercise device for a user, comprising:
  a chest harness comprising:
    a first sleeve positionable around a shoulder and an adjacent armpit of the user;
    a second sleeve positionable around another shoulder and another armpit of the user; and
    a back support connecting a posterior part of the first sleeve and a posterior part of the second sleeve behind the back of the user; and
  a first stretchable strap comprising:
    a first portion attached to the harness; and
    a first handle positioned on the first strap distantly from the first portion of the first strap
  wherein the first strap further comprises a second portion attached to the harness;

wherein the first handle is positioned on the first strap between the first portion of the first strap and the second portion of the first strap; and wherein the first portion of the first strap is attached to a front portion of the first sleeve.

2. The device of claim 1, further comprising a second stretchable strap comprising:
  a first portion attached to the harness; and
  a second handle positioned on the second strap distantly from the first portion of the second strap to allow the user to hold the first handle with one hand and hold the second handle with another hand.

3. The device of claim 1, wherein the back support further comprises a back-support plate positionable against the back of the user.

4. The device of claim 1, wherein the first portion is detachably attached to the harness.

5. The device of claim 1, wherein the first strap comprises an elastic band.

6. The device of claim 1, wherein the first strap is loop-shaped.

7. The device of claim 1, wherein the first portion is attached to the harness by threading the first portion through at least one opening in the harness.

8. The device of claim 1, wherein the first handle is movably positioned on the first strap.

9. The device of claim 1, wherein the first portion of the first strap is attached to the back support.

10. The device of claim 1 further comprising a front chest strap connecting the first sleeve with the second sleeve in front of the user.

11. The device of claim 1, wherein the harness is posture-correcting.

12. An exercise device for a user, comprising:
a chest harness comprising:
  a first sleeve positionable around a shoulder and an adjacent armpit of the user;
  a second sleeve positionable around another shoulder and another armpit of the user; and
  a back support connecting a posterior part of the first sleeve and a posterior part of the second sleeve behind the back of the user; and
a first stretchable continuous-loop-shaped strap threaded through the harness and comprising:
  a first handle positioned on the first strap distantly from the harness; and
  a second handle positioned on the first strap distantly from the first handle and distantly from the harness.

13. The device of claim 12, wherein the first handle is movably positioned on the first strap.

14. The device of claim 12, wherein the back support further comprises a back-support plate positionable against the back of the user.

15. The device of claim 12, wherein the harness is posture-correcting.

16. The device of claim 12 further comprising a front chest strap connecting the first sleeve with the second sleeve in front of the user.

* * * * *